United States Patent [19]

Smeaton

[11] 4,420,254

[45] Dec. 13, 1983

[54] CUVET AND ASSOCIATED APPARATUS AND METHOD FOR USING SAME

[76] Inventor: John R. Smeaton, P.O. Box 337, Wayne, Ill. 60184

[21] Appl. No.: 122,376

[22] Filed: Feb. 19, 1980

[51] Int. Cl.³ .............................................. G01N 1/14
[52] U.S. Cl. ................................. 356/246; 73/864.11
[58] Field of Search ............... 356/246, 244; 250/526; 73/864.11; 435/291, 808

[56] References Cited

U.S. PATENT DOCUMENTS

| | | | |
|---|---|---|---|
| Re. 30,391 | 9/1980 | Liston | 356/246 X |
| 3,622,279 | 11/1971 | Moran | 356/246 X |
| 3,628,682 | 12/1971 | Paulson | 356/246 X |
| 3,786,683 | 1/1974 | Berman et al. | 73/864.11 X |
| 3,860,347 | 1/1975 | Jones | 356/246 |
| 3,865,548 | 2/1975 | Padawer | 435/808 X |
| 3,869,215 | 3/1975 | Nolan | 356/246 |
| 3,961,899 | 6/1976 | Trivedi et al. | 356/246 X |
| 3,999,948 | 12/1976 | Deindoerfer et al. | 356/244 X |
| 4,305,665 | 12/1981 | Achter et al. | 356/339 |

FOREIGN PATENT DOCUMENTS

| | | | |
|---|---|---|---|
| 1417010 | 9/1965 | France | 356/244 |
| 971745 | 9/1964 | United Kingdom | 356/246 |
| 1282357 | 7/1972 | United Kingdom | 356/246 |

Primary Examiner—John K. Corbin
Assistant Examiner—Matthew W. Koren

[57] ABSTRACT

A cuvet with an open upper portion adapted for connection to a source of variable pressure and a lower, sample retaining or window portion having a draw hole and transparent windows. A controlled source of variable pressure is provided with means for releasible connection to the open upper portion of the cuvet. After connection, the variable pressure source is actuated to reduce the pressure in the open upper portion of the cuvet to draw liquid sample through the draw hole and into alignment with the windows. The variable pressure source is also employed to transport and insert the cuvet into a cuvet holder of a spectrophotometer. The pressure is maintained in the cuvet to hold the liquid specimen aligned with the windows while the spectroanalysis is performed. Upon completion of analysis, means associated with the variable pressure source to heat and stir the sample while in the cuvet and to detach the cuvet are respectively provided. In one embodiment the above operations are performed manually through use of a hand-held variable pressure source and in another embodiment they are performed automatically.

13 Claims, 11 Drawing Figures

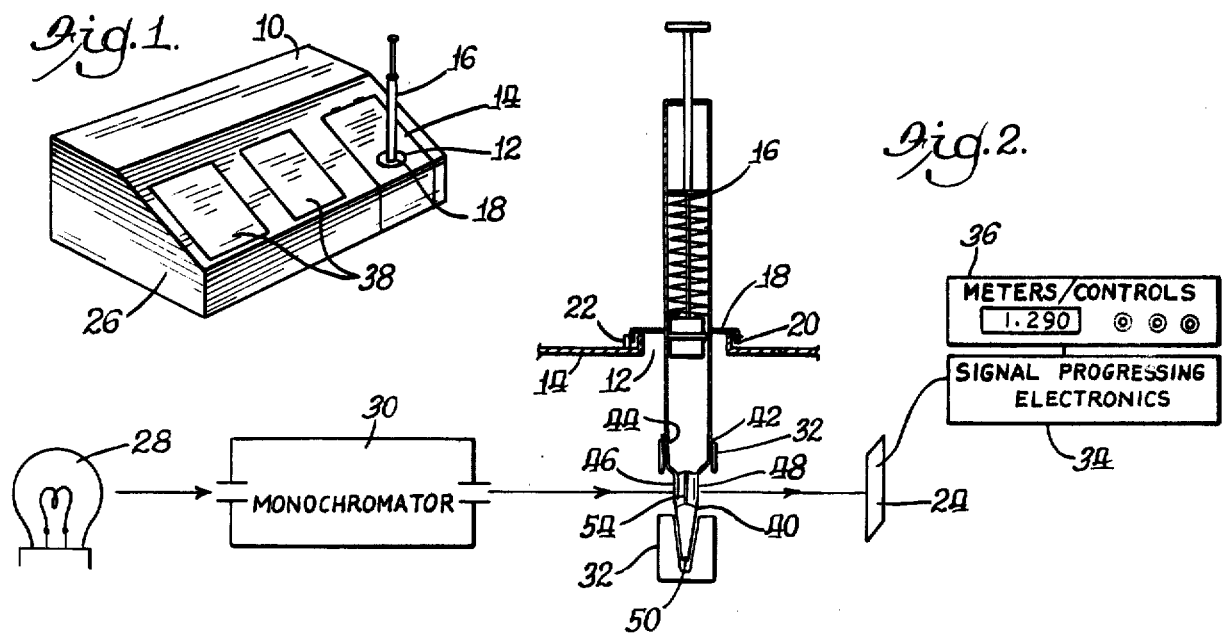
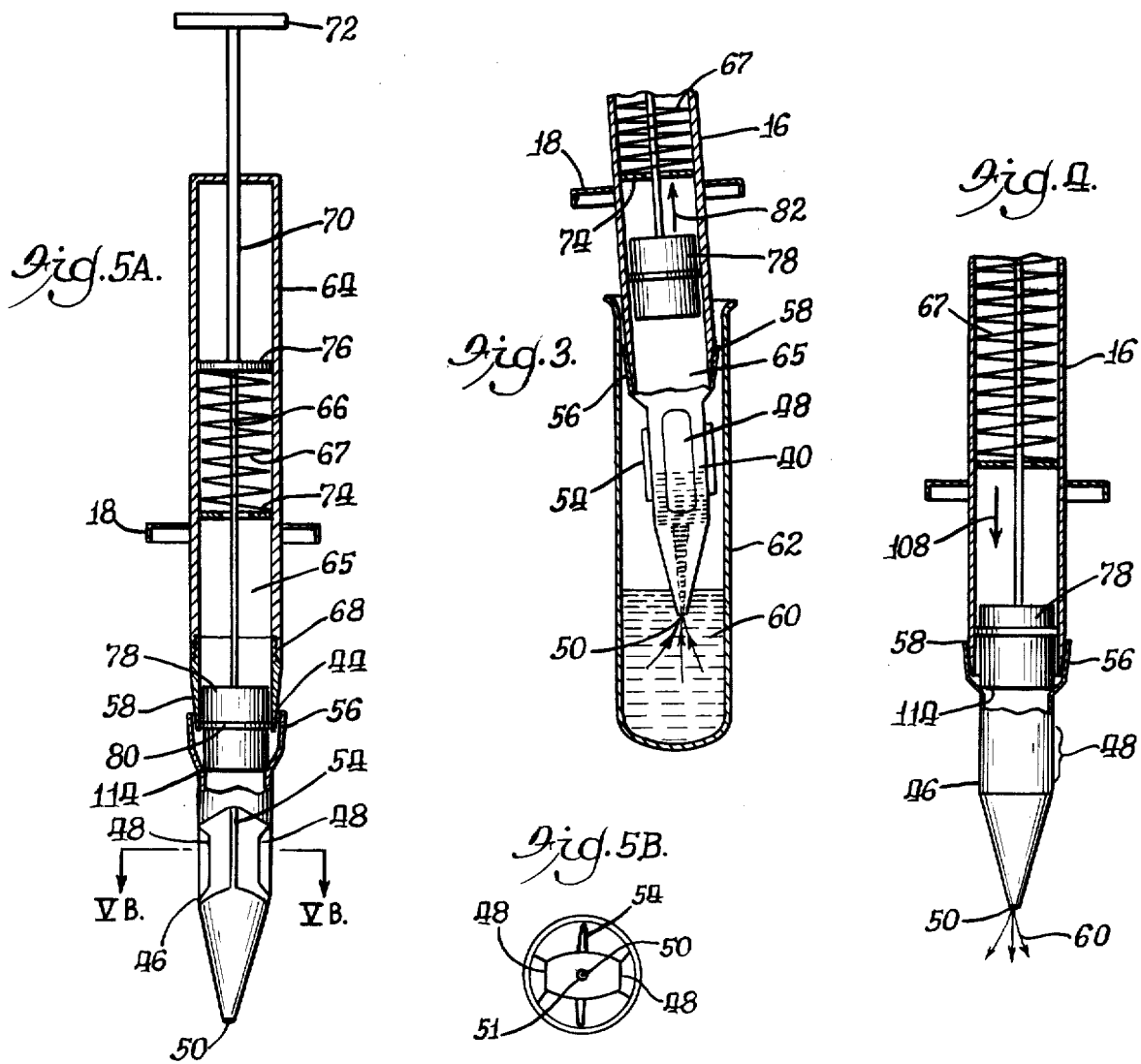

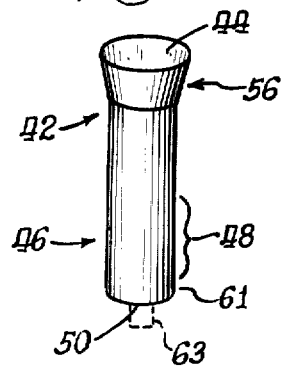
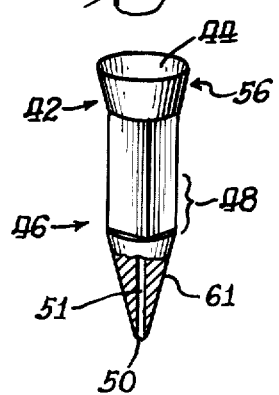
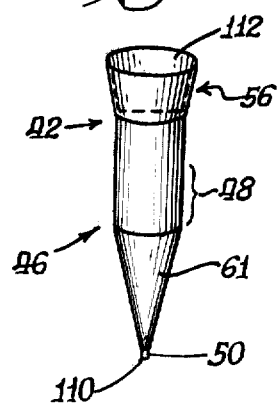
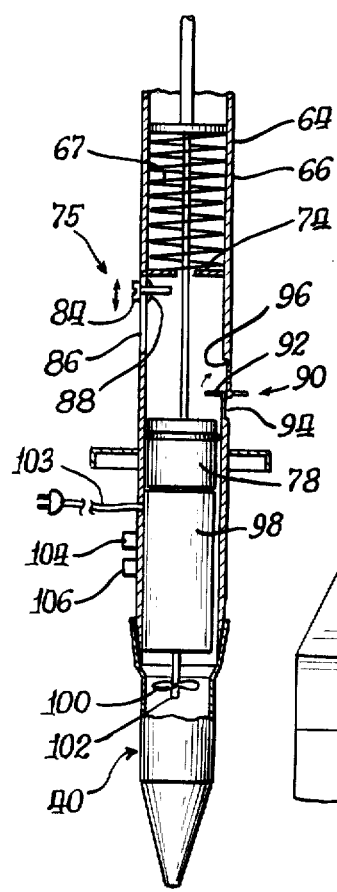
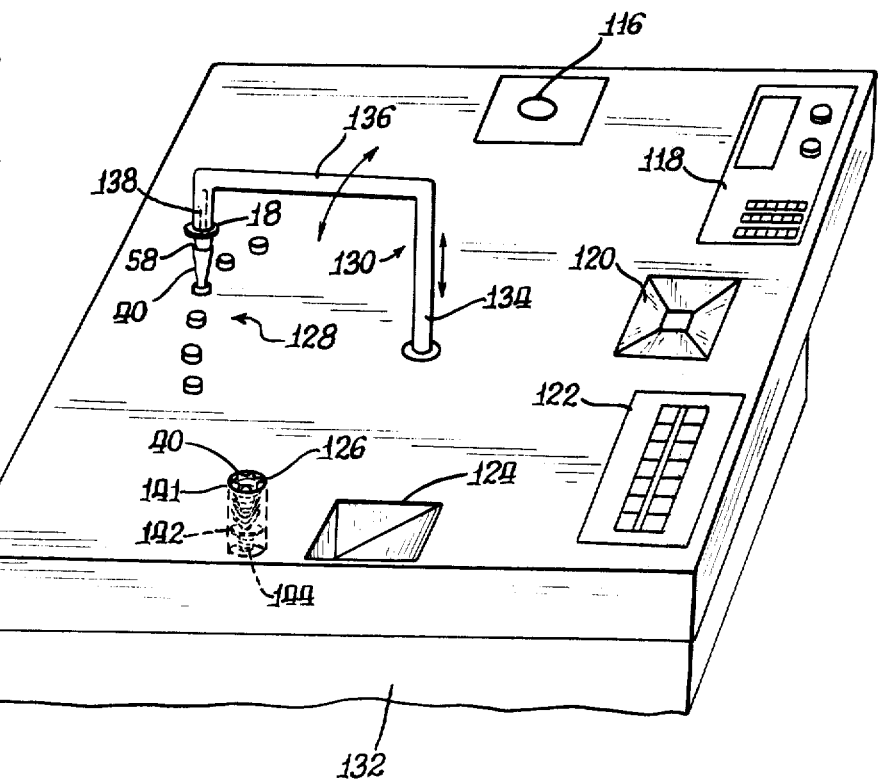

CUVET AND ASSOCIATED APPARATUS AND METHOD FOR USING SAME

BACKGROUND OF THE INVENTION

This invention relates generally to the field of photometric, fluorometric and nephelometric analysis and, more specifically, to a cuvet, and associated apparatus and methods employed in the use of same in association with spectrophotometers, fluorometers, nephelometers and the like.

Current photometric analysis techniques for chemical analysis of blood serum or the like employ spectrophotometers. As described in greater detail in U.S. Pat. No. 3,998,594 of Horne, entitled "Cuvette For Automatic Chemical Testing Apparatus" and issued on an application filed Nov. 26, 1975, common types of spectrophotometers and the like employ removable cells, or cuvets, to contain the sample while the transmittance or other light measurements are being made by the spectrophotometer. Typically, a specimen from a test tube or other reservoir is first deposited into the open top of the cuvet by pouring or by use of a hand-held pipetting device, or pipette, such as shown in U.S. Pat. No. 3,815,790 of Allen and Lee, entitled "Precision Liquid Pipetting Devices" and issued from an application filed Sept. 18, 1972. If not added before, reagent is then often added to the cuvet. It is sometimes necessary to stir or heat, or both stir and heat the resulting mixture of specimen and reagent, or sample, in the cuvet.

The cuvet is then manually placed in a cuvet holder of the spectrophotometer whereat the cuvet and its sample at a transparent window portion, or windows, of the cuvet are interposed between a photoelectric transducer and, except for fluorometric measurements, a source of light of selected wave length, or other radiant source. The transducer produces an electrical signal that has a particular relationship with respect to the amount of light which has been absorbed or transmitted by the sample in the cuvet. The added reagent and light absorbence characteristics for certain types of chemical tests are known and the electrical signal from the transducer is converted to an indication of the constituents present in the sample based upon that knowledge. This information is displayed on meters of the spectrophotometer.

Known cuvets vary in their configuration and material depending on such factors as the degree of accuracy desired, the wavelength of light being used for the spectroanalysis and the mechanical design of the cuvet holder of the particular spectrophotometer being utilized. Traditionally, cuvets have been made of pyrex for use in the visible range of the light spectrum where glass transmits light and have been made of quartz for use in the ultraviolet region. Because of cost, such cuvets are generally used repetitively. In recent years, use of disposable cuvets made of plastic has increased for application in the visible region of the spectrum and in situations where light characteristics of plastic are adequate for the degree of accuracy desired. Reference may be had to the aforementioned U.S. Pat. Nos. 3,998,594 and 3,627,432 of Bergmann, entitled "Reaction Vessel For Use In Photometric Measurements" and issued from an application filed Apr. 29, 1969.

Generally, all cuvets for use with spectrophotometers comprise elongate, open-ended containers with aligned, transparent sections of opposed sidewalls, on their lower portions, which transparent sections are referred to herein as "windows". The windows are often planer wall sections which are visually distinguishable by configuration from the remaining parts of the cuvet, but such is not necessarily the case if great accuracy is not a critical factor. Generally, the entire cuvet is transparent, but functionally, transparency is only required for the windows. The sample is contained in the cuvet between the windows, and the windows are located at a level such that they align with the light source and photoelectric transducer when inserted in the cuvet holder. The distance between the windows, i.e., the thickness of the liquid sample, is generally standardized as 10 millimeters.

For each sample the steps of filling or loading the cuvet, inserting the cuvet in the cuvet holder, stirring and/or heating the sample in the cuvet and then removing and reloading the cuvet are repeated. Thus, each test requires the operator to load the cuvet by pouring in the sample or specimen and reagent from a test tube or the like into its open top or by using a transfer pipette device, such as the type shown in the aforementioned U.S. Pat. No. 3,815,790.

This procedure presents problems or disadvantages. First, because of the relatively small size of the cuvet opening, being on the order of only one centimeter in diameter, pouring liquids into a series of cuvets is tedious and time consuming and presents problems of spillage and resultant contamination due to necessary manual handling. The use of transfer pipettes also presents contamination problems unless a clean pipette is used for each test, since each new sample may contain either a different specimen or a different reagent. The manual handling of the cuvet required by both loading procedures can also cause smudges on the windows which impairs accuracy.

In more recent years, so called "flow through" spectrophotometers have been developed which have a stationary cell that is filled with specimen and reagents while mounted within the spectrophotometer by means of tubal connections. An example of such a device is shown in U.S. Pat. No. 3,869,215 of Nolan, entitled "Sample Cell Assembly Having A Heat Conductive Chamber Surrounded An Electrothermal Heating Layer". In that device the reagent and specimen are entered into the top of the cell through tubal connections, and the sample is drained out of the bottom of the cell upon completion of the test. Other flow-through spectrophotometers are known in which liquid samples are drawn up into the cell by means of pressure. Generally, these devices also have contamination problems because the same cell is repeatedly used for different samples. In addition, measurement problems are caused by development of air bubbles in the sample and the inability to inspect the cell for such air bubbles or contaminants before performance of the measurement. Further, in most flow through spectrophotometers, no means is provided for saving the sample upon completion of the test.

SUMMARY OF THE INVENTION

The principal object of the present invention is to provide a cuvet with a draw hole, associated variable pressure apparatus and method of using same which will facilitate the easy handling and simple loading of such cuvets in association with their use with spectrophotometers and the like.

A cuvet is provided with a first or upper body portion having an opening adapted for releasible connection of the cuvet with a controlled source of variable pressure and a second, lower body portion, or window portion, having a window and a draw hole for passage therethrough of a liquid sample to be drawn into alignment with the windows within the lower body portion. A controlled variable pressure device is provided with coupler means adapted for releasible connection to the cuvet opening. After connection to the variable pressure device, the cuvet is loaded with a sample by actuating the variable pressure device to apply a reduced pressure, or partial vacuum, to the upper portion of the cuvet while the draw hole is immersed in the sample. This causes the sample to be drawn into the lower body portion through the draw hole and into alignment with the windows.

After the cuvet is loaded with a sample, the variable pressure device is used to carry it to the spectrophotometer and insert it into the cuvet holder. The connection with the variable pressure device is maintained during this time to keep the sample with the cuvet. Upon completion of analysis measurements, the variable pressure device is used to carry the cuvet out of the holder. The variable pressure device may then be actuated to increase the pressure to expel the tested sample out of the cuvet through the draw hole. In one embodiment, the above steps are performed manually through use of hand-held variable pressure device. In another embodiment, the variable pressure device is incorporated in a spectrophotometer and the steps of loading, insertion of the cuvet in the cuvet holder and unloading are performed automatically under electronic or other automatic control.

Other features of the invention include provision of a light shield carried by the variable pressure device which blocks ambient light from the cuvet holder when the cuvet is inserted in the holder and provision of means associated with the variable pressure device for stirring, heating, or stirring and heating the sample while in the cuvet. A rack for holding a stack of cuvets is provided to enable attachment to the variable pressure device without manual touching of the cuvet, itself.

As can be appreciated from the above, many of the aforementioned problems of known cuvets and methods of loading and unloading them for use with spectrophotometers are overcome with the present invention. With regard to spectrophotometers which require use of a new cuvet for each new test, the problem of spillage while pouring or transporting a loaded cuvet is eliminated. Also, the number of contacts of the specimen or samples with different containers is minimized to minimize chances of contamination and additional container costs. In addition, use of the variable pressure device facilitates handling of the cuvet to increase operator speed and efficiency and avoids smudging of the windows and contamination caused by manual touching of the cuvet. These advantages are obtained to even a greater degree in the embodiment in which the various steps of the method are automated.

In contrast to spectrophotometers employing flow-through cells, use of the method of the present invention enables visual examination of a loaded cuvet for air bubbles or contaminants before and after measurement. In addition, contamination problems are minimized and sample recovery is achieved more simply and cheaply.

DESCRIPTION OF THE DRAWING

The foregoing features and advantages will be explained in greater detail and further features and advantages will become more apparent from the following description of the preferred embodiments which is given with reference to the several figures of the drawing, in which:

FIG. 1 is a perspective view of an exemplary spectrophotometer with a cuvet of the present invention positioned in the cuvet holder with the hand-held variable pressure device attached thereto;

FIG. 2 is a cross-sectional view of the cuvet, hand held variable pressure device and cuvet holder of FIG. 1 together with a schematic illustration of their relationship with the electronics and other parts of the spectrophotometer;

FIG. 3 is an enlarged, part sectional view of a portion of the hand-held pressure device and cuvet in association with a test tube containing a specimen and illustrating loading of the cuvet from the test tube;

FIG. 4 is another enlarged, part sectional view of the lower portion of the hand-held variable pressure device and cuvet and illustrating ejection of a sample from the cuvet through application of pressure to the cuvet;

FIG. 5A is an enlarged sectional view of the cuvet and hand-held variable pressure device and illustrating their condition during ejection of the cuvet;

FIG. 5B is a view of a section taken along section line VB—VB of the cuvet of FIG. 5A;

FIGS. 6A, 6B and 6C are respective views of different shaped embodiments of the cuvets of the present invention;

FIG. 7 is a sectional view of a portion of another embodiment of the hand-held variable pressure device having releasible and adjustable stops and in which means for stirring and heating the sample in the cuvet test tube are provided; and FIG. 8 is a perspective view of a spectrophotometer incorporating a movably mounted variable pressure device which performs the steps of the method automatically under control of suitable electronics.

DESCRIPTION OF THE PREFERRED EMBODIMENTS

Referring to FIG. 1, the first embodiment of my invention is shown as used with a spectrophotometer 10 which may be conventional except for provision of a cuvet access door 14 with an opening 12 for receipt of the hand-held variable pressure device 16. As more clearly shown in FIG. 2, the variable pressure device 16 carries a light shield 18 of opaque material which snugly fits into a groove 20 of an annular lip 22 around the periphery of opening 12. The light shield is provided principally to prevent ambient light from impinging upon either the cuvet 22 or the photoelectric transducer 24. The light shield 18 could also be mounted at the opening 12. However, it also functions to provide additional lateral and vertical support for the variable pressure device 16 when inserted in opening 12. Preferably, the location of the light shield along the length of the variable pressure device is adjustable by means of a set screw or the like to accommodate its use with different spectrophotometers having cuvet holders located at different distances from the cuvet holder access door 14.

A housing 26 of spectrophotometer 10 contains a light source 28, monochromator 30, a cuvet holder 32, photoelectric transducer 24 and the signal processing electronics 34 schematically illustrated in FIG. 2, all of which are conventional. Meters and controls 36 of FIG. 2 are mounted at suitable panels 38 on the outer face of housing 10.

Referring still to FIG. 2, the variable pressure device 16 is seen to have a cuvet 40 attached to one end which, in turn, is inserted and held within the cuvet holder 32. As discussed above, cuvets vary in material and configuration. The configuration of the interior of the cuvet 40 is selected to minimize the amount of reagent or specimen required to fully load the cuvet. One embodiment of the cuvet 40 is shown in FIGS. 2, 3 and 5A and 5B; another embodiment is shown in FIGS. 4, 7, and three other embodiments are respectively shown in FIGS. 6A, 6B and 6C.

Each of the embodiments of the cuvet 40 do, however, have a number of common features. As seen best in FIGS. 2, 6A, 6B, and 6C, each cuvet has a first or upper body portion 42 with an opening 44 at its free end adapted for releasible connection with the variable pressure device 16 and a second or lower sample receiving body portion 46. The sample receiving portion 46 has transparent window sections or windows 48 on opposed sides of the cuvet and a draw hole 50.

Generally, the cuvets are made entirely of transparent material, but functionally, only the windows 50 need be transparent. Thus, the term "windows" as used herein is intended to mean those opposed transparent sections of the lower body portion sidewalls which are interposed in the path of light beam 52, FIG. 2, between the photoelectric transducer 24 and monochromator 30 when the cuvet 40 is fully inserted in Cuvet holder 32, as illustrated in FIG. 2. The windows may be, but are not necessarily, visually distinguishable from the adjacent portions of the lower body portion 46. The windows may be a planar section in a curved wall for improved optical accuracy, as seen in the embodiments FIGS. 3A, 5A and 5B. Alternately, they may comprise planar sections of a flat wall, as seen in FIGS. 6B, or cylindrical sections in a cylindrical wall, as seen in FIG. 6C.

As seen in the embodiment of the cuvet 40 shown in FIGS. 2, 3, 5A and 5B, the cuvet 40 may be provided with guide fins 54, or alignment tabs, which fit into corresponding slots (not shown) of the cuvet holder 32 to maintain proper alignment of the cuvet 40 and to provide it with lateral or vertical support. The cuvet 40 is also supported laterally and vertically by means of a snug fit of the cuvet 40 within the cuvet holder 32.

The upper body portion 42 has a coupling section 56 intermediate the opening 44 and lower body portion 46 which is adapted for releasible connection with the controlled variable pressure device 16. Preferably, the coupling section is connected with the variable pressure device 16 by means of releasible frictional engagement therewith. However, other means of releasible connections such as variously shown in FIGS. 2-7, the inner wall of the coupling section 56 is tapered outwardly from the axial center of cuvet 40 in the direction from the lower body portion 46 to the opening 44. The degree of this tapering is exaggerated in the drawing for purposes of illustration, and in actuality is preferably on the order of 2°. Although other shapes are feasible, the coupling section has the shape of a truncated cone.

In the preferred embodiment, the coupling means of the variable pressure device 16 is a tapered wall or coupler section 58 at the connection end of the variable pressure device 16. The coupler section 58 has a wall with an inward taper that substantially matches that of the coupling section 56. In making the connection, the coupler section 58 is press-fit into snug frictional engagement with the coupling section 56, as best seen in FIGS. 3 and 4. When in coupling engagement, one or the other, or both, of the coupling section 56 and the coupler section 58 are resiliently distorted and pressed against the other to increase the strength of the frictional mating engagement. As described later with reference to FIG. 8, this manner of making connection can be employed to avoid manual touching of the cuvet itself which can otherwise result in smudging or contamination of the cuvet.

The draw hole 50 is located at the end of the lower body portion 46 of cuvet 40. Referring to FIG. 3, the cuvet 40 is loaded with liquid specimen, reagent or sample by immersing a part of the lower body portion 46 and draw hole 50 into the liquid 60 and then employing the variable pressure device 16 to create a partial vacuum in the upper body portion 42. This partial vacuum causes the liquid 60 to be drawn or sucked through draw hole 50 into the cuvet 40 and in alignment with windows 48.

In order to avoid contact of the liquid 60 with the outside of windows 48, the draw hole 50 is spaced from windows 48. As seen in FIGS. 6B and 6C, lower body portion 46 has a conically shaped section 61 located intermediate the draw hole 50 and windows 48. As seen in FIG. 6A, even when the second body portion is substantially uniform in cross-sectional shape between the first body portion 42 and the draw hole 50, the windows 48 are spaced from draw hole 50. Alternately, with regard to the embodiment of FIG. 6A, the windows 48 could be lowered and a nipple 63 with the draw hole located at its free end added. As best seen in FIG. 6B, the hollow part 51 of lower body portion 61 is reduced in section to minimize to total amount of liquid required to fill the cuvet 40 up to the level of windows 48.

One embodiment of the hand-held variable pressure device 16 is best seen in FIGS. 3, 4 and 5. The device 16 comprises an elongate, cylindrical, hollow body or barrel 64 containing a plunger 66 mounted for reciprocal movement with the barrel 64. The coupler section 58 is carried at one end of barrel 64 and may be integrally formed therewith, as seen in FIGS. 3 and 4. Alternately, the coupler section 58 may be a separate part which is releasibly attached to the end of barrel 64 by means of a screw-type or other type connection 68 to enable different length or different sized or shaped coupler sections 58 to be used with the same barrel 64. The lower portion of the hollow barrel 64 functions at a variable pressure chamber 65.

The plunger 66 is attached to one end of a plunger holder 70, and a finger grip or cap 72 is attached to its other end. A coil spring 67 within barrel 64 is interposed between a stop member 74 and a seat member 76 carried at the juncture of the plunger holder 70 and the plunger 66. The spring 67 biases the plunger toward the withdrawn end of its stroke, as shown in FIG. 2. The free end of plunger 66 carries a tip 78 with a resilient O-ring 80 which resiliently presses against the bore of barrel 64 and of coupling wall section 58 to form a substantially air-tight seal therewith.

Referring to FIGS. 3 and 4, the cuvet 40, when attached to variable pressure device 16, is loaded by immersing draw hole 50 of the empty cuvet 40 into liquid 60 with the plunger 66 in its extended position, as shown in FIG. 4, and then allowing the plunger 66 to move in the direction of arrow 82 toward its withdrawn position until the tip 78 reaches stop member 74. As the tip 78 moves in the direction of arrow 82, a partial vacuum is created in the upper body portion 42 of cuvet 40 which causes the liquid 60 to be drawn or sucked through draw hole 50 and into the lower body portion 46.

The amount of liquid which is drawn into the cuvet 40 depends, in part, upon the length of the withdrawal stroke of plunger 66. Different size cuvets may require different amounts of liquid. Accordingly, as seen in another embodiment of hand-held variable pressure device 16 of FIG. 7, an adjustable stop member 75 is provided. Adjustable stop member 75 comprises a screw 84 which extends through an elongate slot 86 in the side of barrel 64 and which is screwed through a threaded, nut-like fastener 88 tight against the wall of barrel 64. The stop member 75 is adjusted by simply loosening screw 84 and relocating it to a different location along the length of slot 86 and re-tightening the screw at that location.

The cuvet 40 may also be provided with a releasible stop 90. Releasible stop 90 comprises a stop member 92 mounted to the side of barrel 64 for movement into and out of blocking relationship with tip 78. The stop member is spring-biased into its blocking position as shown in FIG. 7. When it is desired to release the stop 90, the portion of the stop member 92 external of barrel 64 is pressed into a slot 94 to pivot the portion of stop member 92 located at the inside of barrel 64 into a slot 96. The tip is then allowed to continue its travel toward its withdrawn position until blocked by adjustable stop member 75 or non-adjustable stop member 70.

The releasable stop 90 is used when it is desired to successively load different preselected amounts of liquid into different cuvets. Alternately, it may be employed to successively load the same cuvet 40 with two different liquids, such as specimen and reagent. The cuvet draw hole 50 is immersed in one liquid and then plunger 66 withdrawn until the tip 78 is blocked by the releasible stop 90. After loading the first liquid, the cuvet is withdrawn from the first liquid and the draw hole 50 is immersed in the second liquid. The releasible stop member 92 is then pivoted out of blocking engagement with tip 78 to allow it to travel to the next stop to load a selected amount of the second liquid. Depending upon the degree of test accuracy desired, the outside of the cuvet may be cleaned after loading the first liquid to prevent contamination of the second liquid.

In the embodiment of FIG. 7, a miniature electric motor and a battery supply therefor within a housing 98 are mounted at the inside of the barrel 64. The electric motor drives a miniature rotary stirring member 100 to mix the sample while in the cuvet. The battery (not shown), in addition to powering the electric motor, powers a heating element 102 to heat the sample while in the cuvet.

Alternately, the motor and heating element 102 may be powered externally by means of suitable electrical connection 103 with an external power supply. Two push-button switches 104 and 106 are provided for respectively controlling the operation of the heating element 102 and the stirring member 100.

Referring to FIG. 4, after the test on the sample has been completed, the liquid 60 may be expelled out of the cuvet 40 through draw hole 50. This is done by pushing plunger 66 in the direction of arrow 108 to increase the pressure in cuvet 40.

As illustrated in FIG. 6C, if it is desired to keep the sample, the sample may be stored in the cuvet 40 itself by plugging the draw hole 50 with a resilient plug 110, detaching the cuvet 40, and then plugging the cuvet opening 44 with a stopper 112.

The variable pressure device 16 is provided with means for ejecting or detaching the cuvet 40. In this regard, the cuvet 40 is provided with an annular shoulder 114 or other reduced section intermediate the opening 44 and the lower body portion 46. The diameter of the bore at the shoulder 114 or other reduced section is less than that of the end of tip 78. The variable pressure device 16, in turn, is designed for movement of the end of tip 78 past the free end of the coupler section 58. When so extended, the tip 78 butts against the shoulder 114, as shown in FIG. 4, to push or eject the cuvet 40 off the end of coupler section 58, as illustrated in FIG. 5A.

The hand-held variable pressure device 16 and cuvets 40 of the present invention are used in the following manner in conjunction with a spectrophotometer to perform spectroanalysis. First, the cuvet 40 is attached to the variable pressure device 16 by pressing the coupler section 58 into coupling frictional engagement with the coupling section 56. The variable pressure device 16 is then used to carry the cuvet 40 to the reservoir of liquid or succession of liquids to be loaded into the cuvet 40 whereat the cuvet 40 is loaded through draw hole 50, as described above. After loading, the cuvet 40 is carried by means of the variable pressure device 16 to the cuvet holder 32 of the spectrophotometer and seated into the cuvet holer 32, as illustrated in FIG. 2. Upon completion of the test, the variable pressure device 16 and cuvet 40 are withdrawn from the cuvet holder 32.

The liquid 60 may then be ejected out of the draw hole 50 into a suitable waste or storage recepticle in the manner described with reference to FIG. 4. Alternately, if desired to store the test sample in the cuvet 40, plug 110 and stopper 112, as seen in FIG. 6C, may be employed. If not, the cuvet 40 may be ejected from the variable pressure device 16, as described with reference to FIG. 5A.

Referring to FIG. 8, another embodiment of my invention is shown in which an automatically controlled variable pressure device is incorporated with a spectrophotometer and the above steps are performed automatically under control of suitable electronics. The details of such type electronic controls form no part of the present invention, but reference may be had to U.S. Pat. 3,909,203 of Young, et al., entitled "Analysis System Having Random Identification Labelling System", issued from an application filed Aug. 4, 1974, for an illustration of a general type of control suitable for the spectrophotometer of FIG. 8.

Briefly, the spectrophotometer of FIG. 8 comprises a cuvet holder 116; a meter and control panel 118 at which are mounted the readout meter and necessary controls for spectroanalysis; a liquid disposal reservoir 120; a control panel 122 to which is mounted programing controls for performance of the steps of the method; a cuvet disposal 124; a cuvet rack 126; an array of liquid reservoirs 128 for holding specimens, reagent or sample; and a controlled variable pressure device connectable through a movably mounted tubular arm 130 to a cuvet 40. The controlled variable pressure device and electronic control (not shown) are mounted within a suitable housing 132.

The arm 130 has a vertical section 134 mounted for both vertical movement along its elongate axis and rotary movement about its axis. An L-shaped section 136 has a light shield 18 and carries the coupler section 58 at its free end for attachment to cuvet 40. Contained within the down-turned portion of L-shaped section 136 is an extendible arm 138 which is controlled by the electronic control to extend out of the end of the coupler section 58 to detach a cuvet 40 at the proper time. The arm 138 is used in the same manner that the tip 78 is used in the hand-held variable pressure device 16 to push the cuvet 40 of the coupler section 58. Also, mounted with the down-turned portion and extending or extendible into cuvet 40 are the heating element 102 and stirring element 100.

The end of section 134 is coupled to the variable pressure device mounted within housing 132 which is controlled by the electronic controls. The variable pressure device may comprise a device similar to the hand-held variable pressure device 16 in combination with servomotors or the like to move the plunger 66 in response to the electronic controls to apply variable pressure to the cuvet 40, as needed.

The arm 130 and variable pressure device 16 are controlled to perform the steps of the method as described below.

First, the arm 130 is moved to the cuvet rack 126 while in its raised position. It is then lowered to cause the coupler section 58 to be inserted and frictionally coupled with the top cuvet 40 in the rack 126. The rack 126 has a housing 140 which contains a plurality of cuvets 40 stacked one inside the other and underlying a resilient retainer 141. The stack of cuvets 40 are supported on a platform 142 which, in turn, is supported on a coil spring 144 located intermediate the bottom of housing 140 and platform 142. The coil spring acts as a shock absorber and also functions to keep the top cuvet 40 accessible near the top of the rack 126. It should be appreciated that rack 126, whether mounted within or without the spectrophotometer, can also be employed for connecting cuvets 40 to the hand-held variable pressure device 16 to avoid smudging or contamination of cuvet 40 caused by manual handling.

After the connection has been made, the arm 130 with the cuvet 40 attached thereto is raised out of the rack 126 and then moved to a position overlying a preselected one of the liquid reservoirs. This preselection is made by means of switches at control panel 122. The arm 130 is then lowered to cause the draw hole 50 to be immersed in the selected liquid, and then the selected amount of partial vacuum is supplied to load the cuvet through the draw hole 50. The arm 130 is then raised to withdraw the loaded cuvet 40 from the liquid reservoir 128. If it is desired to load another liquid into the same cuvet, then arm 130 is rotated to a position over the next selected liquid reservoir 128, and the above loading process is repeated with additional pressure vacuum being applied.

Upon completion of all loading, the raised arm 130 is rotatably moved until the cuvet 40 is located over the cuvet holder 116. The arm is then lowered to seat the cuvet 40 into the cuvet holder. While the arm 130 moves to cuvet holder 116, the stirring member 102, the member 100, or both, may be actuated. The stirring or heating may also be done after insertion into the cuvet holder 116.

Upon completion of stirring, the spectroanalysis test is performed. Upon completion of the test, the arm 130 is raised to remove the cuvet 40 from the cuvet holder 116 and then rotatably moved to locate the cuvet 40 over the disposal reservoir 120. At this location, the variable pressure device is actuated to increase the pressure in the top of the cuvet 40 to expel the tested sample into the disposal reservoir 120. Alternately, if it is desired to preserve the sample in its cuvet, the operator may insert a stopper 110, detach the cuvet 40, and insert a stopper 112.

If the cuvet is not detached at the disposal reservoir 120, then the arm 130 is caused to rotatably move to a position at which the cuvet 40 overlies cuvet disposal shute 124. Arm 138 is then actuated to eject or detach the cuvet 40 off the arm and into the shute. The arm 130 is then moved to its position over cuvet rack 126, and the process may then be repeated for the next test.

The controls at control panel 122 may include means for manually stepping the spectrophotometer through the above operation but preferably, the electronic controls are programed to automatically perform these steps without further operator input beyond preselecting the liquid reservoirs 128. Thus, a single operator may be capable of simultaneously operating more than one of the spectrophotometers of FIG. 8 at the same time.

While specific embodiments of the various features of the present invention have been disclosed, it should be appreciated that many variations can be made without parting from the scope of the invention, as defined in the followed claims.

I claim:
1. The combination of:
   a cuvet comprising a hollow body with first and second body portions, said first body portion having an opening and an associated coupling section for releasible connection thereof with a variable pressure device, and said second body portion having windows and a draw hole for receipt therethrough of a liquid to be drawn into the second body portion and in alignment with the windows;
   a variable pressure device, said variable pressure device having a hollow body, means for varying the pressure within said hollow body and means releasibly coupling the hollow body with the cuvet opening;
   a spectrophotometer; a cuvet holder; an access panel having an opening for receipt of the variable pressure device; and
   a light shield, said variable pressure device extending through said opening, and said light shield substantially closing against light any gap between the variable pressure device and the sides of the opening.
2. The combination of claim 1 in which said light shield is carried by the variable pressure device.
3. An automated spectrophotometer comprising:
   a controlled source of variable pressure;
   a cuvet holder;
   means for releasibly connecting said controlled source of variable pressure to a cuvet at a location spaced from said cuvet holder;
   means mounted for movement of said cuvet releasibly connecting means to insert a cuvet connected thereto into said cuvet holder for spectroanalysis of a sample contained therein and for removal of said cuvet from the cuvet holder when the analysis is complete.

4. The automated spectrophotometer of claim 3 including a liquid disposal reservoir, said releasibly connecting means mounted for movement of a cuvet connected thereto to a location overlying said disposal reservoir to expel any liquid contained in the cuvet into said reservoir.

5. The automated spectrophotometer of claim 3 including a reservoir for containing a liquid sample to be tested, said releasibly connecting means being mounted for movement of a cuvet connected thereto into said reservoir.

6. The automated spectrophotometer of claim 3 including means for holding a plurality of cuvets, said releasible connecting means being mounted for movement into releasible connection with and removal of one of said plurality of cuvets.

7. The automated spectrophotometer of claim 3 including a cuvet disposal chute, said releasibly connecting means being mounted for movement of a cuvet connected thereto to a location overlying said cuvet disposal chute and including means for ejecting a cuvet from said connecting means and into said chute.

8. The automated spectrophotometer of claim 3 in which said releasibly connecting means includes means for stirring a liquid contained in a cuvet connected thereto.

9. The automated spectrophotometer of claim 3 in which said releasibly connecting means is mounted for rotary movement.

10. The automated spectrophotometer of claim 9 in which said releasibly connecting means is mounted for vertical movement of a cuvet connected thereto.

11. A method of loading a cuvet with a liquid comprising the steps of:
   releasibly connecting the open end of a cuvet having a draw hole with a variable pressure device;
   immersing the draw hole into the liquid;
   producing a sufficient partial vacuum in the cuvet to draw the liquid through the draw hole and into the cuvet to a desired window level;
   placing the cuvet in a cuvet holder of a spectrophotometer; and
   using the spectrophotometer to perform spectroanalysis of the specimens;
   removing the cuvet from the cuvet holder when analysis is completed by ejecting the cuvet from the variable pressure device; and
   repeating the above steps of the method with a new cuvet.

12. The method of claim 11 in which said steps are performed manually.

13. The method of claim 11 in which said steps are performed automatically.

* * * * *